(12) United States Patent
Gagnon et al.

(10) Patent No.: US 12,076,083 B2
(45) Date of Patent: Sep. 3, 2024

(54) AUTOMATED SLIT LAMP SYSTEM AND METHOD OF EXAMINING AN EYE USING SAME

(71) Applicant: LIGHTX INNOVATIONS INC., Chambly (CA)

(72) Inventors: Jean-Mathieu Gagnon, Chambly (CA); Sébastien Gagne, Blainville (CA)

(73) Assignee: LIGHTX INNOVATIONS INC., Chambly (CA)

( * ) Notice: Subject to any disclaimer, the term of this patent is extended or adjusted under 35 U.S.C. 154(b) by 647 days.

(21) Appl. No.: 17/089,820

(22) Filed: Nov. 5, 2020

(65) Prior Publication Data

US 2021/0127967 A1 May 6, 2021

Related U.S. Application Data

(60) Provisional application No. 62/931,234, filed on Nov. 6, 2019.

(51) Int. Cl.
| | |
|---|---|
| A61B 3/00 | (2006.01) |
| A61B 3/135 | (2006.01) |
| A61B 3/15 | (2006.01) |

(52) U.S. Cl.
CPC ........... *A61B 3/0008* (2013.01); *A61B 3/135* (2013.01); *A61B 3/152* (2013.01)

(58) Field of Classification Search
CPC ........ A61B 3/0008; A61B 3/135; A61B 3/152
USPC .................................................. 351/221, 225
See application file for complete search history.

(56) References Cited

U.S. PATENT DOCUMENTS

| | | | |
|---|---|---|---|
| 5,870,167 A | 2/1999 | Knopp | |
| 7,854,510 B2 | 12/2010 | Verdooner | |
| 8,998,411 B2 | 4/2015 | Tumlinson | |
| 10,092,183 B2 | 10/2018 | Berestka | |
| 2014/0211163 A1* | 7/2014 | Maruyama | A61B 3/135 351/214 |
| 2014/0368793 A1* | 12/2014 | Friedman | A61B 3/107 351/221 |
| 2016/0095515 A1* | 4/2016 | Bor | A61B 3/14 351/246 |

(Continued)

FOREIGN PATENT DOCUMENTS

CA 2730720 C 1/2018

*Primary Examiner* — Sharrief I Broome
(74) *Attorney, Agent, or Firm* — Norton Rose Fulbright Canada LLP

(57) ABSTRACT

There is described an automated slit lamp system for imaging an eye of a patient. The automated slit lamp system generally has: an illuminator emitting an illumination beam towards the eye of the patient during examination, the illuminator being operable to illuminate the eye of the patient in different illumination patterns; a controller communicatively coupled to the illuminator, the controller controlling the illuminator to automatically illuminate the eye of the patient with a sequence of illumination patterns comprising at least a first illumination pattern and a second illumination pattern being different from the first illumination pattern, the first and second illumination patterns being selected from a group comprising: diffuse illumination, direct focal illumination, tangential illumination, retroillumination, indirect illumination and sclerotic scatter illumination; and a camera generating images of the eye during both the first and second illumination patterns.

7 Claims, 10 Drawing Sheets

(56) References Cited

U.S. PATENT DOCUMENTS

| | | | |
|---|---|---|---|
| 2016/0095516 A1* | 4/2016 | Nara | A61B 3/156 |
| | | | 351/214 |
| 2017/0156591 A1* | 6/2017 | Berestka | A61B 3/14 |
| 2018/0153399 A1* | 6/2018 | Fink | A61B 3/0008 |
| 2020/0288976 A1* | 9/2020 | Okuda | A61B 3/1233 |
| 2021/0153740 A1* | 5/2021 | Oomori | A61B 3/024 |

* cited by examiner

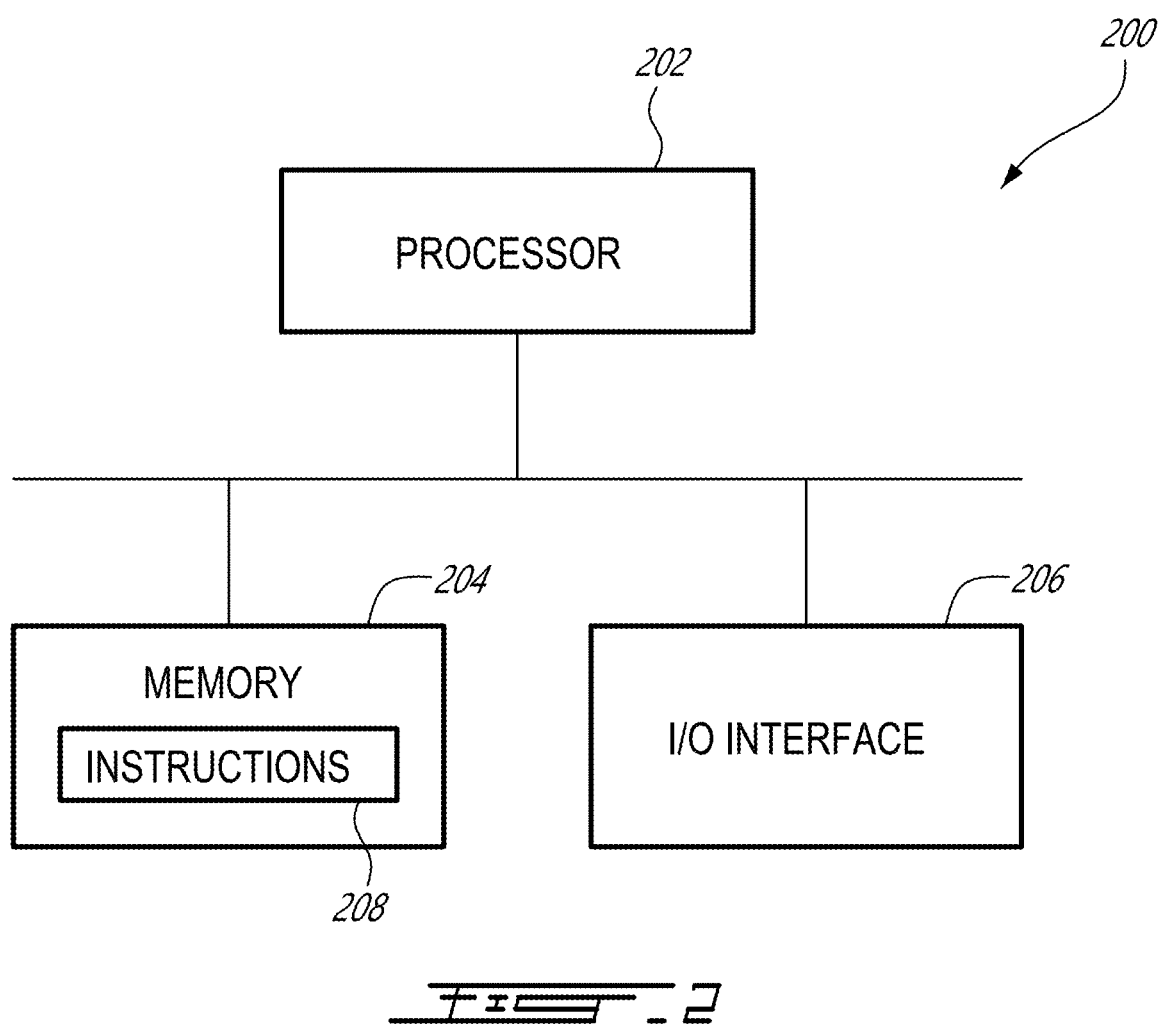

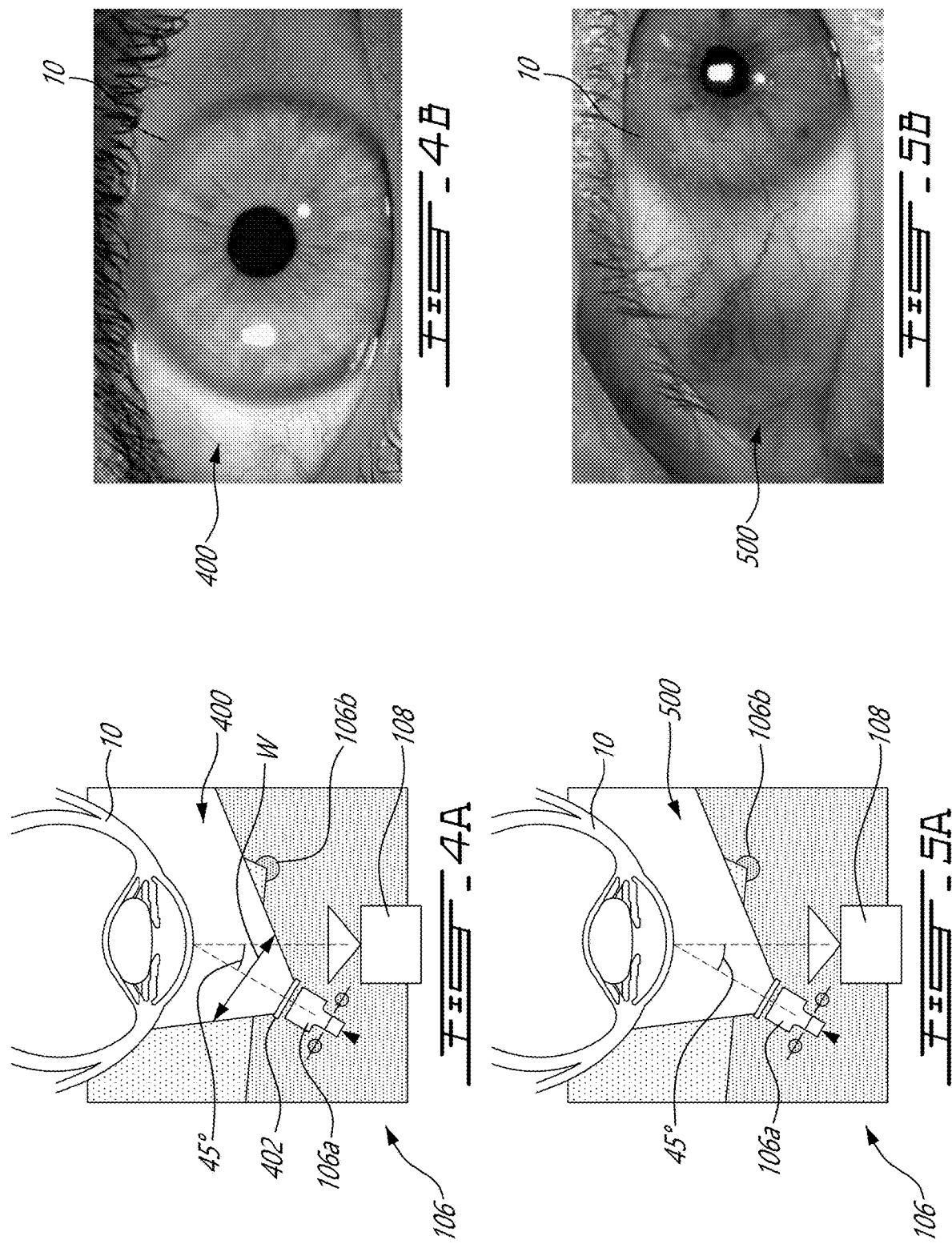

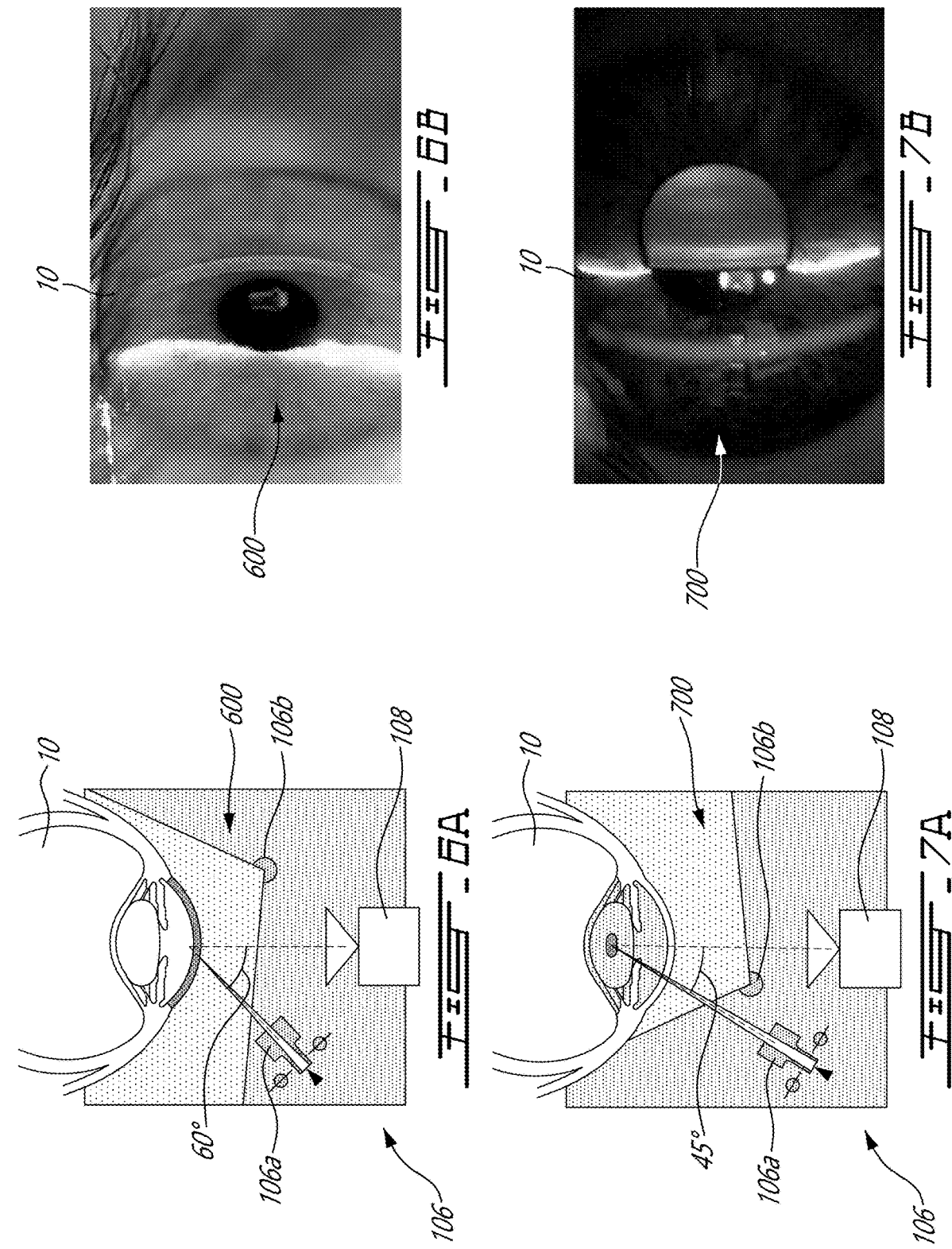

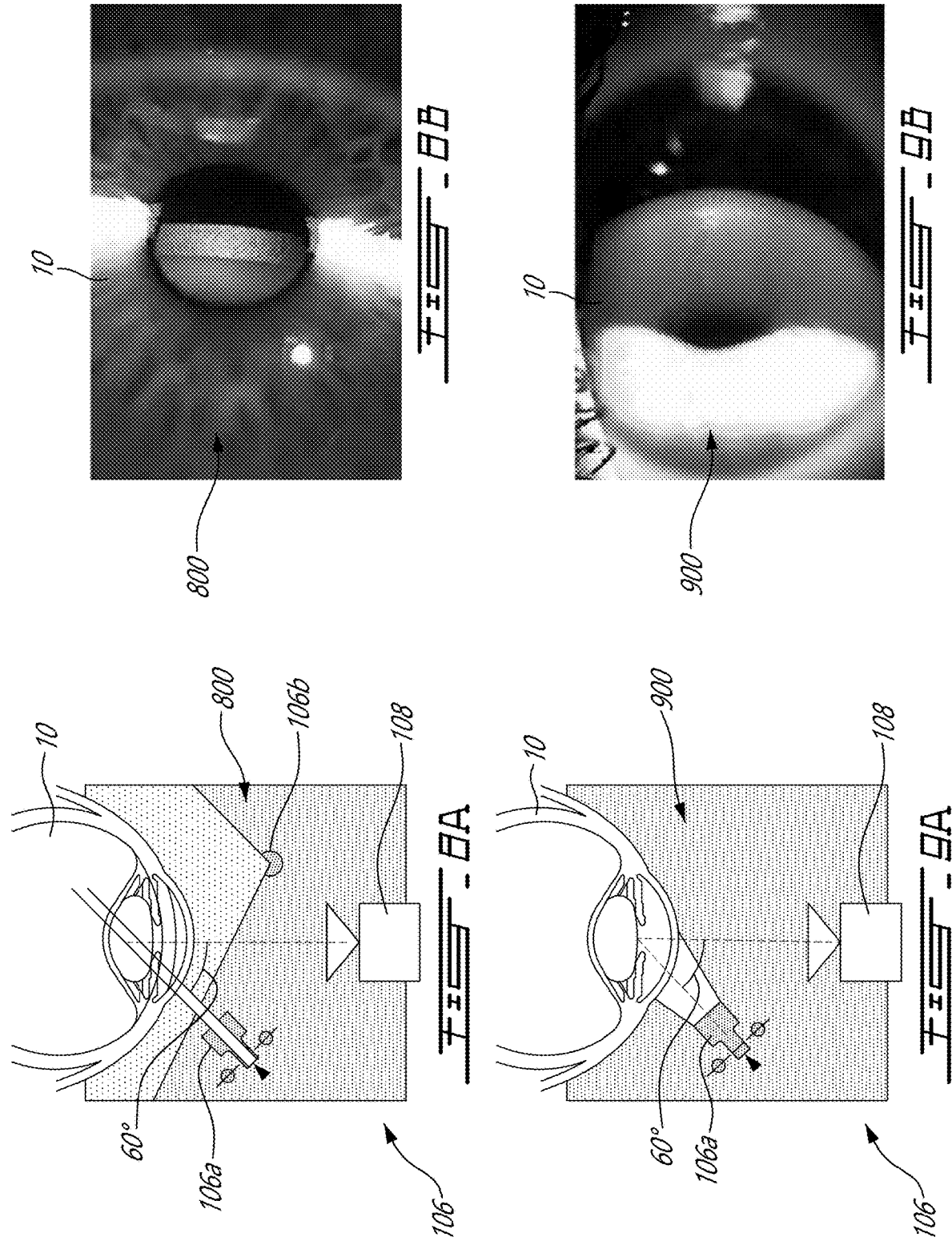

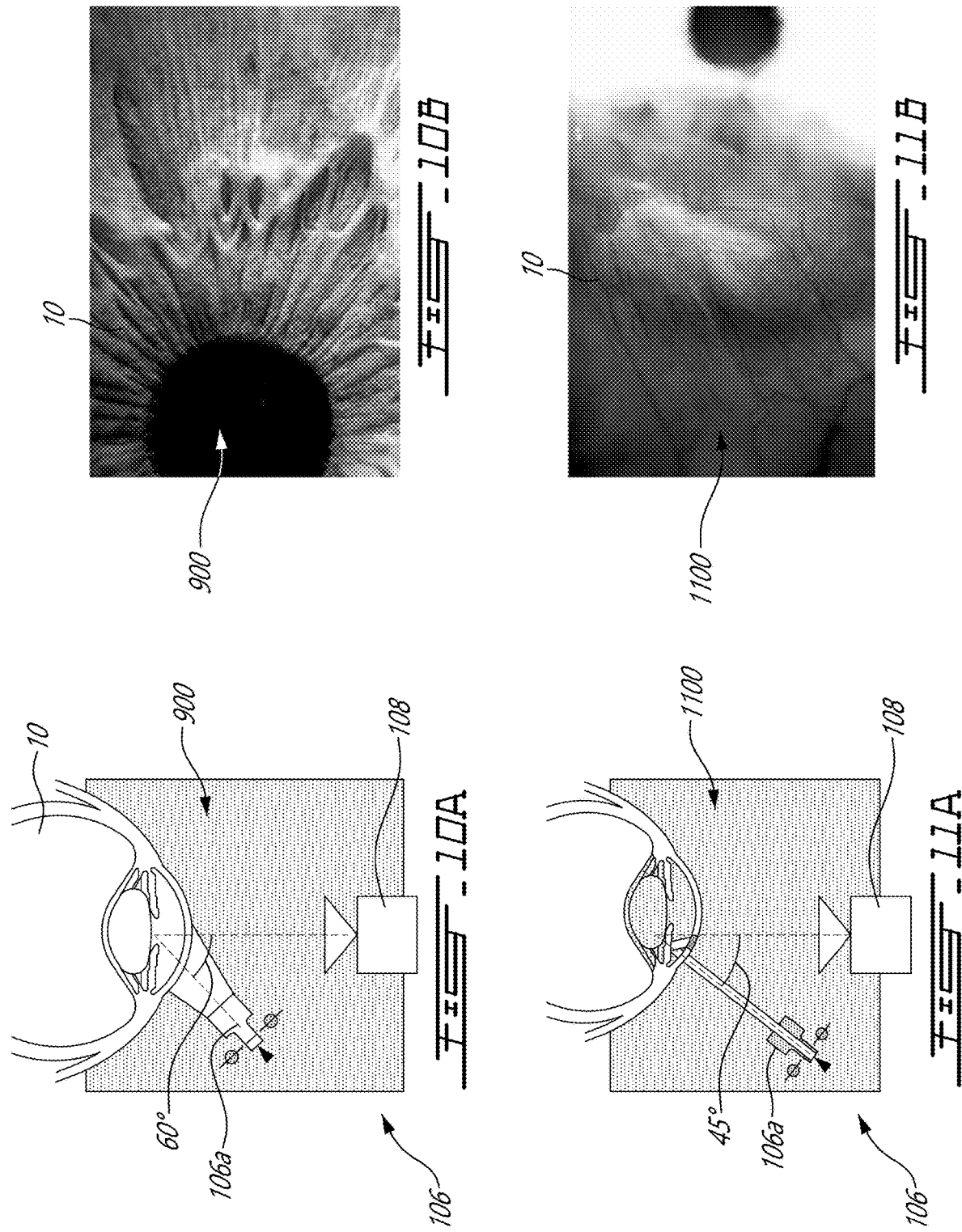

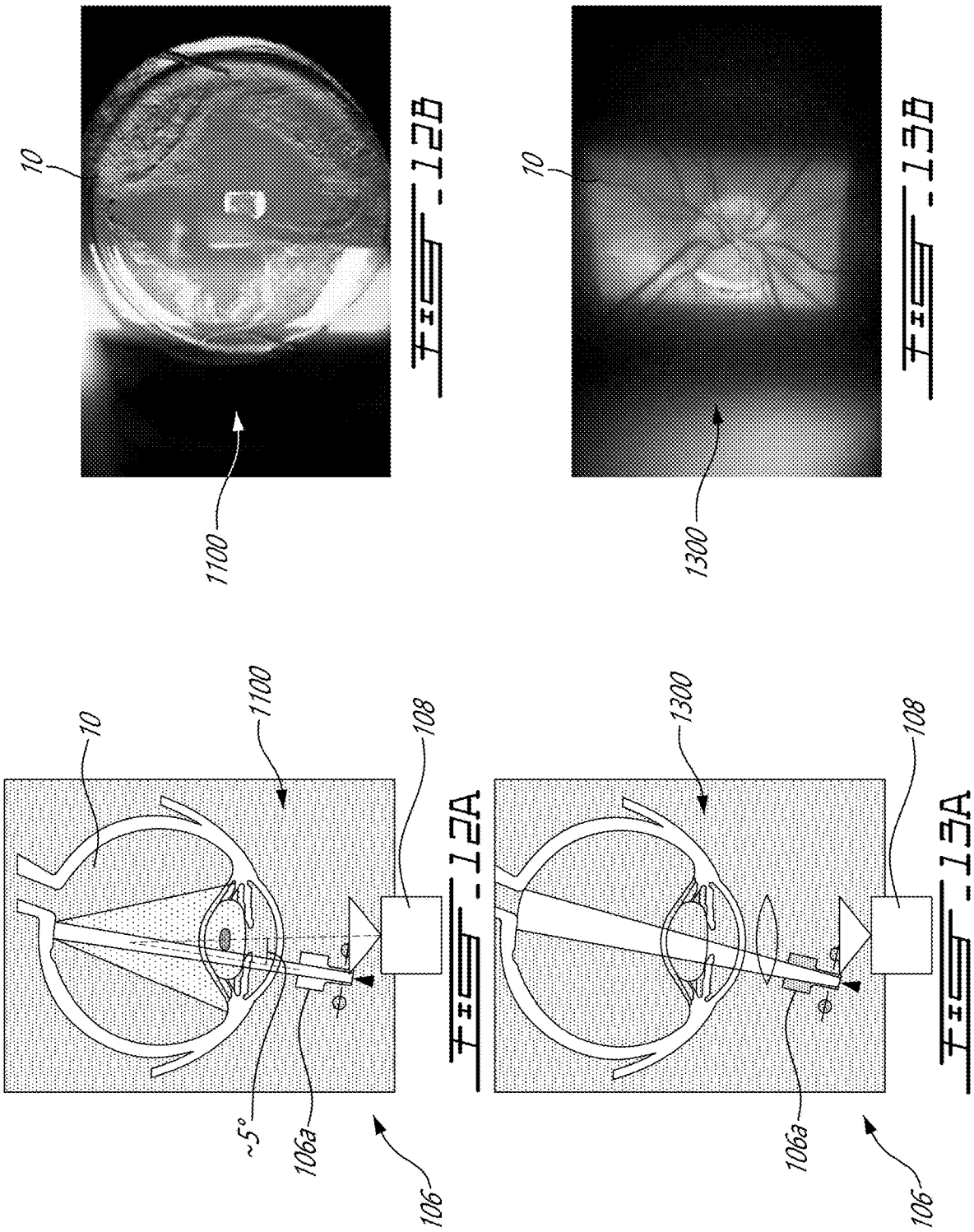

AUTOMATED SLIT LAMP SYSTEM AND METHOD OF EXAMINING AN EYE USING SAME

FIELD

The improvements generally relate to eye examination and more specifically relates to eye examination using slit lamps.

BACKGROUND

A slit lamp is an instrument having an illumination source that can be shaped as a thin strip of light and shined into the eye of a patient, and a microscope for observing the so-illuminated eye for examination purposes. Slit lamps are generally operated by optometrists, ophthalmologist and other eye care professionals as they generally require a high level of training to illuminate some specific parts of the eye in precise conditions, which can be challenging. Although existing slit lamps are satisfactory to a certain degree, there remains room for improvement.

SUMMARY

In an aspect, there is provided an automated slit lamp system having a frame, a face receiving assembly mounted to the frame and receiving a face of a patient during examination, an illuminator configured to illuminate an eye of the patient with a plurality of different illumination patterns, a controller controlling the illuminator to illuminate the eye of the patient with a sequence of different illumination patterns, and a camera to generate images of the eye when so-illuminated. The illumination patterns are selected from a group comprising: diffuse illumination, direct focal illumination, tangential illumination, retroillumination, indirect illumination and sclerotic scatter illumination. Accordingly, by illuminating the eye with the above-mentioned sequence of different illumination patterns while generating images of the so-illuminated eye, the need of highly trained optometrists, ophthalmologist and other eye care professionals to operate the slit lamp can be greatly reduced as the acquisition of the eye images is automated thus reducing the need for highly trained professional(s) and consequently, the examination of the images can be performed in a remote or delayed fashion providing tele-ophthalmology possibilities to the eye-care specialist.

In accordance with a first aspect of the present disclosure, there is provided an automated slit lamp system for imaging an eye of a patient, the automated slit lamp system comprising: a frame; an illuminator mounted to the frame and emitting an illumination beam towards the eye of the patient, the illuminator being operable to illuminate the eye of the patient in a plurality of different illumination patterns; a controller communicatively coupled to the illuminator, the controller having a processor and a memory having stored thereon instructions which when executed by the processor perform the steps of: controlling the illuminator to automatically illuminate the eye of the patient with a sequence of illumination patterns comprising at least a first illumination pattern and a second illumination pattern being different from the first illumination pattern, the first and second illumination patterns being selected from a group comprising: diffuse illumination, direct focal illumination, tangential illumination, retroillumination, indirect illumination and sclerotic scatter illumination; and a camera mounted to the frame and generating a plurality of images of the eye during both the first and second illumination patterns.

Further in accordance with the first aspect of the present disclosure, the controller can for example be communicatively coupled to the camera, the instructions further comprising receiving the plurality of images from the camera.

Still further in accordance with the first aspect of the present disclosure, the instructions can for example further comprise associating a first set of the received images to the first illumination pattern and associating a second set of the received images to the second illumination pattern.

Still further in accordance with the first aspect of the present disclosure, the instructions can for example further comprise generating time stamps indicating at least one of beginnings and ends of the first and second illumination patterns, said associating being performed based on said time stamps.

Still further in accordance with the first aspect of the present disclosure, the camera can for example be a three-dimensional camera.

Still further in accordance with the first aspect of the present disclosure, the three-dimensional camera can for example be a light field imaging camera.

Still further in accordance with the first aspect of the present disclosure, said sequence of illumination patterns can for example further comprise a third illumination pattern being different from the first and second illumination patterns, the third illumination pattern being selected from a group comprising: diffuse illumination, direct focal illumination, tangential illumination, retroillumination, indirect illumination and sclerotic scatter illumination.

Still further in accordance with the first aspect of the present disclosure, said sequence of illumination patterns can for example further comprise a fourth illumination pattern being different from the first, second and third illumination patterns, the fourth illumination pattern being selected from a group comprising: diffuse illumination, direct focal illumination, tangential illumination, retroillumination, indirect illumination and sclerotic scatter illumination.

Still further in accordance with the first aspect of the present disclosure, said sequence of illumination patterns can for example further comprise a fifth illumination pattern being different from the first, second, third and fourth illumination patterns, the fourth illumination pattern being selected from a group comprising: diffuse illumination, direct focal illumination, tangential illumination, retroillumination, indirect illumination and sclerotic scatter illumination.

Still further in accordance with the first aspect of the present disclosure, said sequence of illumination patterns can for example further comprise a sixth illumination pattern being different from the first, second, third, fourth and fifth illumination patterns, the fourth illumination pattern being selected from a group comprising: diffuse illumination, direct focal illumination, tangential illumination, retroillumination, indirect illumination and sclerotic scatter illumination. Still further in accordance with the first aspect of the present disclosure, the automated slit lamp system can for example further comprise a face receiving assembly mounted to the frame and receiving a face of the patient.

Still further in accordance with the first aspect of the present disclosure, the automated slit lamp system can for example further comprise an eye sensor mounted to the frame, the eye sensor detecting a presence of the face of the patient in said face receiving assembly, and generating a signal indicating that said sequence of illumination patterns can be initiated.

In accordance with a second aspect of the present disclosure, there is provided a method of imaging an eye of a patient using a slit lamp, the method comprising: a controller receiving a sequence of illumination patterns comprising at least first and second illumination patterns being different from another, the first and second illumination patterns being selected from a group comprising: diffuse illumination, direct focal illumination, tangential illumination, retroillumination, indirect illumination and sclerotic scatter illumination; the controller modifying an illuminator of the slit lamp in preparation of said first illumination pattern; the illuminator illuminating the eye according to said first illumination pattern; a camera generating a first set of images of the eye during said first illumination pattern; the controller modifying the illuminator in preparation of said second illumination pattern; the illuminator illuminating the eye according to said second illumination pattern; and the camera generating a second set of images of the eye during said second illumination pattern.

Further in accordance with the second aspect of the present disclosure, the method can for example further comprise the controller associating the first set of images to the first illumination pattern and associating the second set of images to the second illumination pattern.

Still further in accordance with the second aspect of the present disclosure, said associating can for example further comprise generating time stamps indicating at least one of beginnings and ends of the first and second illumination patterns, said associating being performed based on said time stamps.

Still further in accordance with the second aspect of the present disclosure, said sequence of illumination patterns can for example include a third illumination pattern being different from the first and second illumination patterns, the method further comprising: the controller modifying the illuminator in preparation of the third illumination pattern; the illuminator illuminating the eye according to said third illumination pattern; and the camera generating a third set of images of the eye during said third illumination pattern, the third illumination pattern being selected from a group comprising: diffuse illumination, direct focal illumination, tangential illumination, retroillumination, indirect illumination and sclerotic scatter illumination.

Still further in accordance with the second aspect of the present disclosure, the method can for example further comprise, prior to said modifying, detecting a presence of the face of the patient, and generating a signal indicating that said method can be performed.

Still further in accordance with the second aspect of the present disclosure, said steps can for example be performed during an examination of the eye of the patient, the controller can for example further generate an output of said examination based at least of said first and second sets of images.

In accordance with a third aspect of the present disclosure, there is provided an automated slit lamp system for imaging an eye of a patient, the automated slit lamp system comprising: a frame; an illuminator mounted to the frame and operable to illuminate the eye of the patient in a plurality of different illumination patterns based on a number of adjustable parameters; an indicator mounted to the frame and proximate to the illuminator, the indicator being configured to indicate predetermined parameters associated to a given illumination pattern, wherein when the adjustable parameters of the illuminator are manually set to the predetermined parameters the illuminator illuminates the eye of the patient with the given illumination pattern; a controller communicatively coupled to the indicator, the controller having a processor and a memory having stored thereon instructions which when executed by the processor perform the steps of: indicating a first series of predetermined parameters of the illuminator for illumination of the eye of the patient according to a first illumination pattern; and after said indicating the first series of predetermined parameters, indicating a second series of predetermined parameters of the illuminator for illumination of the eye of the patient according to a second illumination pattern; the first and second illumination patterns being different from one another and being selected from a group comprising: diffuse illumination, direct focal illumination, tangential illumination, retroillumination, indirect illumination and sclerotic scatter illumination.

Further in accordance with the third aspect of the present disclosure, said controller can for example be communicatively coupled to the illuminator, said instructions can for example further comprise controlling the illuminator to automatically illuminate the eye of the patient with a sequence of illumination patterns comprising at least the first illumination pattern and the second illumination pattern.

Still further in accordance with the third aspect of the present disclosure, the indicator can for example be provided in the form of a display screen of a mobile electronic device.

Still further in accordance with the third aspect of the present disclosure, the mobile electronic device can for example have a camera generating a plurality of images of the eye during both the first and second illumination patterns.

Still further in accordance with the third aspect of the present disclosure, the mobile electronic device can for example be removably mounted to the frame using a mount.

Many further features and combinations thereof concerning the present improvements will appear to those skilled in the art following a reading of the instant disclosure.

DESCRIPTION OF THE FIGURES

In the figures,

FIG. 2 is a schematic view of an example of a computing device of the controller of FIG. 1, in accordance with one or more embodiments;

FIG. 4A is a top plan view of an example of an automated slit lamp system, shown in a first diffuse illumination pattern, in accordance with one or more embodiments;

FIG. 4B is an exemplary image of an eye generated during the first diffuse illumination pattern of FIG. 4A;

FIG. 5A is a top plan view of an example of an automated slit lamp system, shown in a second diffuse illumination pattern, in accordance with one or more embodiments;

FIG. 5B is an exemplary image of an eye generated during the second diffuse illumination pattern of FIG. 5A;

FIG. 6A is a top plan view of an example of an automated slit lamp system, shown in a first direct focal illumination pattern, in accordance with one or more embodiments;

FIG. 6B is an exemplary image of an eye generated during the first direct focal illumination pattern of FIG. 6A;

FIG. 7A is a top plan view of an example of an automated slit lamp system, shown in a second direct focal illumination pattern, in accordance with one or more embodiments;

FIG. 7B is an exemplary image of an eye generated during the second direct focal illumination pattern of FIG. 7A;

FIG. 8A is a top plan view of an example of an automated slit lamp system, shown in a third direct focal illumination pattern, in accordance with one or more embodiments;

FIG. 8B is an exemplary image of an eye generated during the third direct focal illumination pattern of FIG. 8A;

FIG. 9A is a top plan view of an example of an automated slit lamp system, shown in a first tangential illumination pattern, in accordance with one or more embodiments;

FIG. 9B is an exemplary image of an eye generated during the first tangential illumination pattern of FIG. 9A;

FIG. 10A is a top plan view of an example of an automated slit lamp system, shown in a second illumination pattern, in accordance with one or more embodiments;

FIG. 10B is an exemplary image of an eye generated during the second tangential illumination pattern of FIG. 10A;

FIG. 11A is a top plan view of an example of an automated slit lamp system, shown in a first retroillumination pattern, in accordance with one or more embodiments;

FIG. 11B is an exemplary image of an eye generated during the first retroillumination pattern of FIG. 11A;

FIG. 12A is a top plan view of an example of an automated slit lamp system, shown in a second retroillumination pattern, in accordance with one or more embodiments;

FIG. 12B is an exemplary image of an eye generated during the second retroillumination pattern of FIG. 12A;

FIG. 13A is a top plan view of an example of an automated slit lamp system, shown in a 90-diopter lens illumination pattern, in accordance with one or more embodiments;

FIG. 13B is an exemplary image of an eye generated during the 90-diopter lens illumination of FIG. 13A;

DETAILED DESCRIPTION

Figure 1:
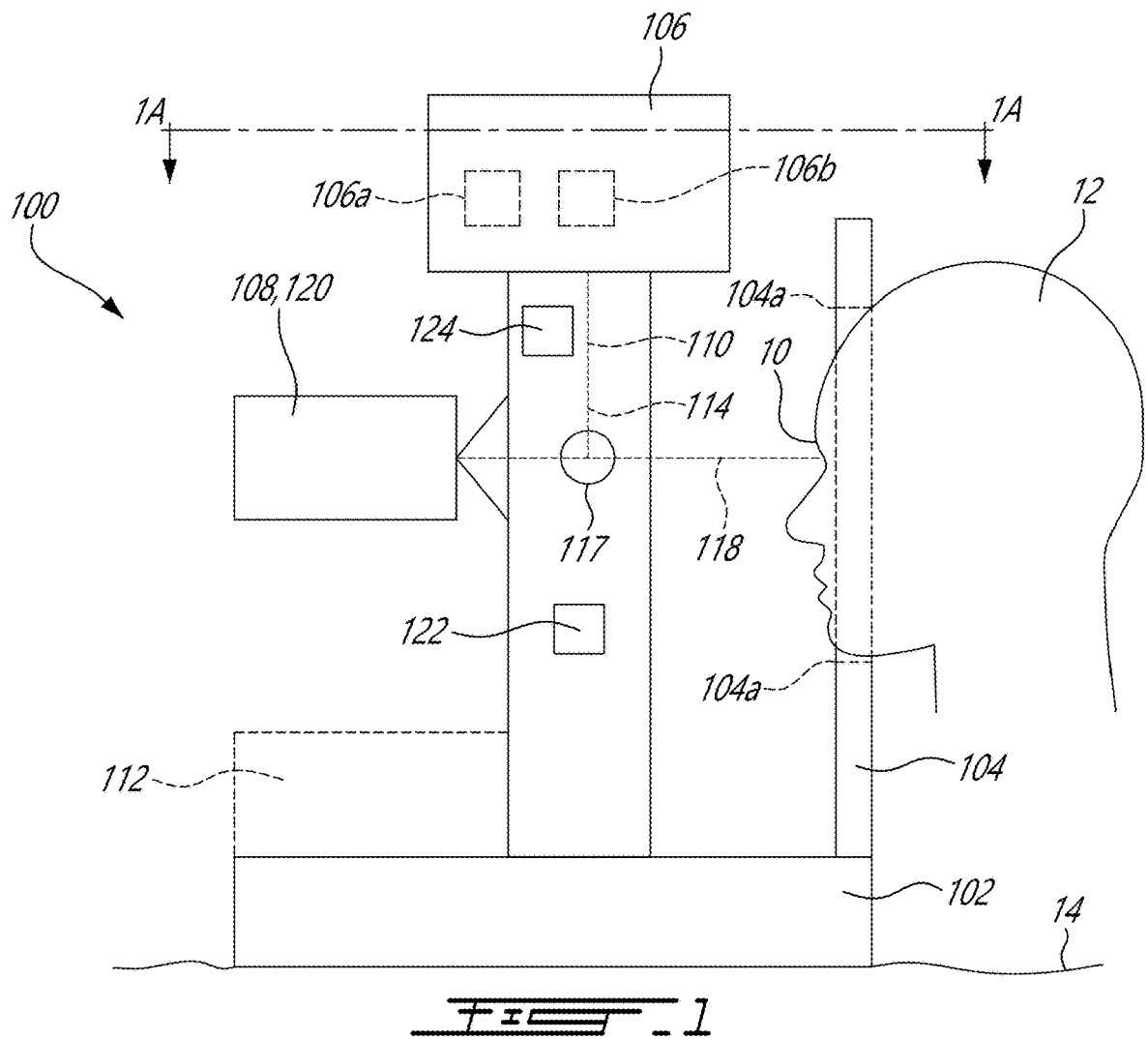
FIG. 1 is a schematic side view of an example of an automated slit lamp system, shown with an illuminator, a camera and a controller, in accordance with one or more embodiments.

FIG. 1 shows an example of an automated slit lamp system 100 for imaging an eye 10 of a patient 12 for examination purposes, for instance. As depicted, the automated slit lamp system 100 has a frame 102 to which are mounted a face receiving assembly 104, an illuminator 106, and a camera 108.

As shown in this example, the face receiving assembly 104 receives a face of the patient 12 during examination. The face receiving assembly 104 can be supported or otherwise fixed to a surface 14 such as a table, depending on the embodiment. The face receiving assembly 104 can have a forehead support 104a and/or a chin support 104b to comfortably receive the face of the patient 12. The forehead and chin supports 104a and 104b can be adjustable to suitably receive the face of the patient 12.

It is intended that the illuminator 106 emits an illumination beam 110 towards the face received in the face receiving assembly 104 during the examination, and more specifically towards the eye 10 of the patient 12. The illuminator 106 is operable to illuminate the eye 10 of the patient 12 in a plurality of different illumination patterns. The illuminator 106 can include a slit illuminator 106a and a background illuminator 106b in some embodiments. The illuminator 106 can be positioned above the head of the patient 12, such as in Haag Streit type slit lamps, or below the head of the patient 12, such as in Zeiss type slit lamps.

As shown in this specific example, a controller 112 mounted to the frame 102 is communicatively coupled to the illuminator 106. However, in some other embodiments, the controller 112 may not be mounted to the frame 102. Indeed, the controller 112 may be remote from the frame 102. During examination, the controller 112 controls the illuminator 106 to illuminate the eye 10 of the patient 12 automatically with a sequence of illumination patterns comprising at least a first illumination pattern and a second illumination pattern, the first and second illumination patterns being different from one another. It is intended that the first and second illumination patterns are selected from a group comprising: diffuse illumination, direct focal illumination, tangential illumination, retroillumination, indirect illumination and sclerotic scatter illumination, examples of which are described below with reference to FIGS. 4A to 14A. In some embodiments, the controller 112 controls the illuminator 106 to illuminate the eye 10 of the patient in more than two successive illumination patterns.

Still referring to FIG. 1, the camera 108 of the automated slit lamp system 100 generates a plurality of images of the eye 10 during both the first and second illumination patterns. In some embodiments, the so-generated images can be communicated to a network or stored on a memory for later consultation by trained optometrists, ophthalmologist and other eye care professionals.

In some embodiments, the camera 108 can be a three-dimensional (3D) camera 120 configured to generate 3D images of the so-illuminated eye. For instance, the 3D camera can be a stereoscopic camera in some embodiments as the 3D camera 120 can be a light field camera (also referred to as "plenoptic camera" in the field) in some other embodiments. An example of such light field camera is manufactured by Raytrix GmbH, Germany. Other examples of 3D cameras can also be used, as will be apparent to the skilled reader.

It is sought that, in some embodiments, the automated slit lamp system 100 can have an eye sensor 122 mounted to the frame 102. The eye sensor 122 can be a capacitive sensor, an infrared sensor, a range sensor, a camera such as camera 108 or 3D camera 120 and any other suitable type of presence sensor. In some embodiments, it was found preferably to implement the eye sensor 122 using the camera 108 and/or the 3D camera 120. The eye sensor 122 can detect a presence of the face of the patient 12 and generate a signal indicating that the imaging of the eye can be initiated, e.g., that the sequence of illumination patterns can be initiated. It is noted that the eye sensor 122 can be embodied by a face recognition module, which can be partially or wholly implemented by the controller 112, using the image(s) acquired by the camera 108 or the camera 120. Accordingly, in some embodiments, the eye sensor 122 not only detects the face of the patient but also determines whether the eye is open, suitably positioned, and ready for image acquisition. This determination can be made using the images continuously generated by the camera 108, the 3D camera 120, in some embodiments. In such an embodiment, face sensing would not be performed using a standalone sensor, but rather using the camera 108 and a face recognition and/or calibration algorithm(s) ran by the controller 112 or any other type of computing device. The face recognition and/or calibration algorithm(s) can be conventional computer vision algorithm(s), machine learning algorithm(s) and any other suitable type of face recognition and/or calibration algorithm(s). In case the camera 108 is the three-dimensional camera 120, face recognition algorithm(s) may be easier to implement as the three-dimensional camera can provide depth information in each 3D image. In some embodiments, the three-dimensional camera 120 is a stereo-camera using one or more algorithms to detect the presence of the eye and also the eye structure such as the iris and lens contour(s) amongst other structures to detect the face, the eye and the precise alignment of the system to trigger the illumination sequence.

Additionally or alternatively, the eye sensor 122 may also detect whether the eye 10 of the patient is satisfactorily positioned relative to the illumination and imaging paths 114 and 118. Accordingly, in some embodiments, the automated slit lamp system 100 can have a display 124 to display instructions to operator, e.g., a health care professional. Examples of such instructions can be to turn the eye leftward or rightward, to tilt the eye upward or downward, translate the eye downward, upward, leftward and/or rightward and the like. The display 124 can be configured to display a target to the patient, and possibly also some instructions to look at the displayed target. The target to look may move within the display 124 depending on the illumination pattern to be produced on the eye of the patient.

In such embodiments, the eye sensor 122 and display 124 may all be communicatively coupled with the controller 112 which may receive the signal from the eye sensor 122 and instruct the display 124 to display some predetermined instructions. In some other embodiments, the eye sensor 122 can be omitted. For instance, in these embodiments the eye sensor 122 can be replaced by a push button, or any other type of input, which can be activated upon a technician confirming that the eye 10 of the patient 12 is suitably received in the face receiving assembly 104 and ready for examination.

In some embodiments, it is envisaged that the camera 108 can be movable relative to the face of the patient. For instance, the camera 108 may be mechanically connected to the frame 102 via an articulated arm, or any other suitable type of actuator. In such embodiments, the camera 108 can be moved in any given coordinate system x, y, z relative to the eye of the patient. Accordingly, by moving the camera 108 during examination, one or more images of the eye of the patient can be taken from different spatial positions while the eye is being illuminated by one or more of the illumination patterns. The movement of the camera 108 can be controlled by the controller 112.

Figure 1A:
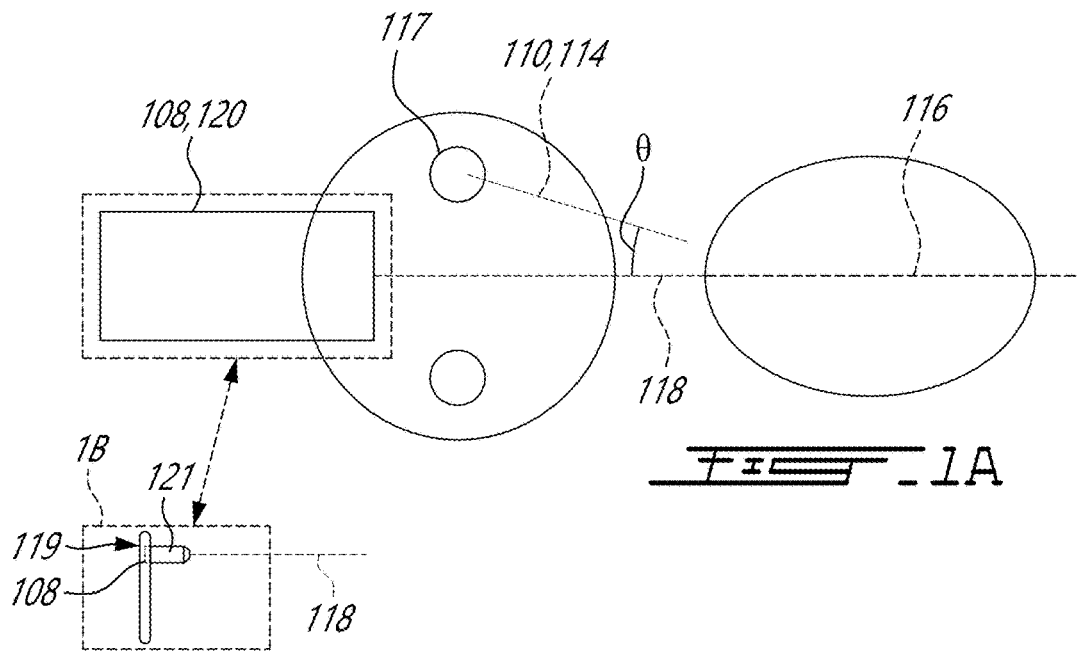
FIG. 1A is a top view of the automated slit lamp system of FIG. 1, taken along section 1A-1A of FIG. 1.

As best shown in FIG. 1A, the illuminator 106 can be configured to illuminate the eye 10 of the patient 12 with the illumination beam 110 along a given illumination path 114. In some embodiments, the illumination path 114 forms an incident angle θ with a sagittal plane 116 of the head of the patient 12. The illumination path 114 can be redirected from a substantially vertical orientation to a substantially horizontal orientation via one or more mirrors 117. In the illustrated embodiment, the camera 108 has an imaging path 118 which originates from the eye 10 of the patient 12 and leads to the camera 108. The illumination and imaging paths 114 and 118 are oversimplified in FIGS. 1 and 1A for ease of understanding. It is intended that the illumination and imaging paths 114 and 118 can be more complex in some other embodiments. As such, the illuminator 106 can include a variety of other optical components, such as shutter(s), mirror(s), diffuser(s), filter(s) and the like to propagate, guide and/or modify the light generated by the illuminator 106, and more specifically by the slit illuminator 106a and the background illuminator 106b in this specific example.

In some embodiments, the camera 108 can be part of a portable electronic device 119 such as shown at inset 1B of FIG. 1A. In these embodiments, the camera 108 of the portable electronic device 119 can be can be optically coupled to a microscope objective 121 aligned along the imaging path 118. The portable electronic device 119 may be maintained into a fixed position relative to the imaging path 118 using a mount (not shown). In some embodiments, the mount is fixed relative to the frame of the automated slit lamp system 100. Examples of such portable electronic device can include, but not limited to, a smart phone, an electronic tablet and the like. In some embodiments, more than one portable electronic device 119 may be mounted in a fixed position relative to the imaging path 118 for image generation purposes. In these embodiments, the cameras of the portable electronic devices can be used in conjunction with one another to capture three-dimensional images of the eye of the patient during any desired illumination pattern. Accordingly, more than one portable electronic device mount may be used in these embodiments. The portable electronic device(s), and their respective camera(s), may be communicatively coupled to the controller via a wireless connection and/or a wired connection. The portable electronic device(s) may be removably mounted to the frame. In some embodiments, one or more buttons proximate to the frame, and in communication with the cameras of the portable electronic devices, may be used to trigger the generation of image(s) by the camera(s) of the portable electronic device(s). Such button(s) may be provided on a table near the operator or on the floor so as to be either activatable by hand or foot, respectively.

The controller 112 can be provided as a combination of hardware and software components. The hardware components can be implemented in the form of a computing device 200, an example of which is described with reference to FIG. 2. Moreover, the software components of the controller 112 can be implemented in the form of a software application, an example of which is described with reference to FIG. 3.

Referring to FIG. 2, the computing device 200 can have a processor 202, a memory 204, and I/O interface 206. Instructions 208 for illuminating the eye 10 of the patient 12 with a predetermined sequence of different illumination patterns can be stored on the memory 204 and accessible by the processor 202.

The processor 202 can be, for example, a general-purpose microprocessor or microcontroller, a digital signal processing (DSP) processor, an integrated circuit, a field programmable gate array (FPGA), a reconfigurable processor, a programmable read-only memory (PROM), or any combination thereof.

The memory 204 can include a suitable combination of any type of computer-readable memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface 206 enables the computing device 200 to interconnect with one or more input devices, such as mouse(s), keyboard(s), camera(s), face sensor(s), eye sensor(s), or with one or more output devices such as display(s), network(s), memory(ies).

Each I/O interface 206 enables the controller 112 to communicate with other components, to exchange data with other components, to access and connect to network resources, to server applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. WMAX), SS7 signaling network, fixed line, local area network, wide area network, and others, including any combination of these.

Figure 3:
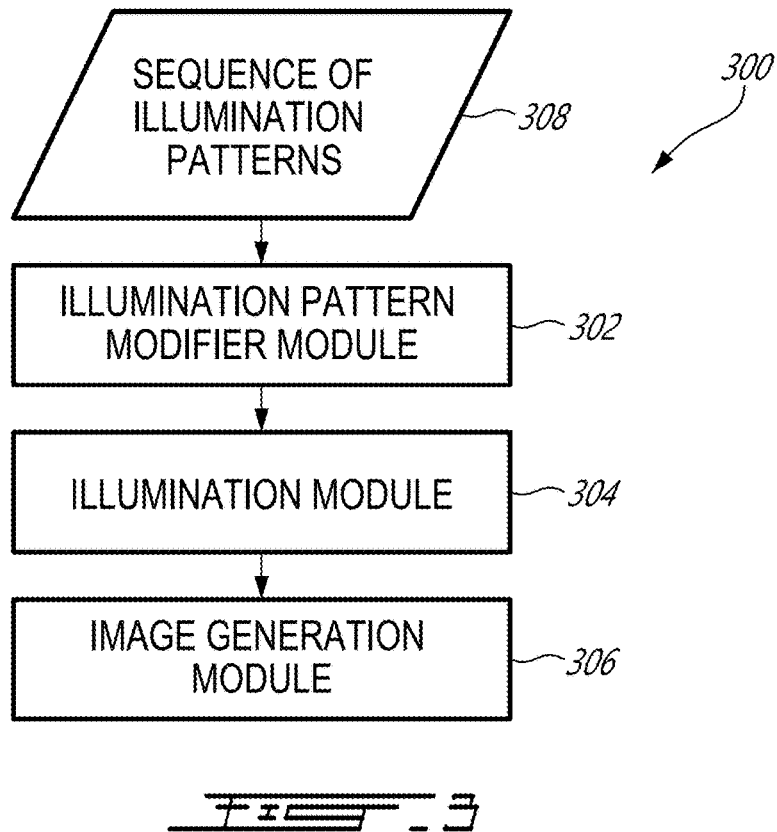
FIG. 3 is a block diagram of an example of a software application of the controller of FIG. 1 configured to perform a method of imaging an eye using the automated slit lamp system of FIG. 1, in accordance with one or more embodiments.

Referring now to FIG. 3, the software application 300 is configured to receive signal(s) and/or data being indicative of the instructions 208 and to determine the instructions 208 upon processing the signal(s) and/or data. In some embodiments, the software application 300 is stored on the memory 204 and accessible by the processor 202 of the computing device 200.

As shown, the software application 300 can have an illumination pattern modifier module 302, an illumination module 304 and an image generation module 306. As shown, the illumination pattern modifier module 302 can receive a given sequence of illumination patterns 308 from a network, memory or any sort of database(s). As such, the illumination pattern modifier module 302 can send instructions to the illuminator 106 to modify its parameters in preparation of a first one of the illumination patterns of the sequence 308. Once the parameters of the illuminator are set in accordance with the first illumination pattern, the illumination module 304 can instruct the illuminator 106 to illuminate the eye 10 of the patient 12 according to the first illumination pattern. During the illumination, the image generation module 306 can receive data from the camera and generate corresponding images of the eye 10 of the patient 12. These modules can interact as such until images have been generated for all the illumination patterns of the sequence 308. The sequence of illumination patterns can include two, three or more different illumination patterns depending on the embodiment.

Figure 3A:
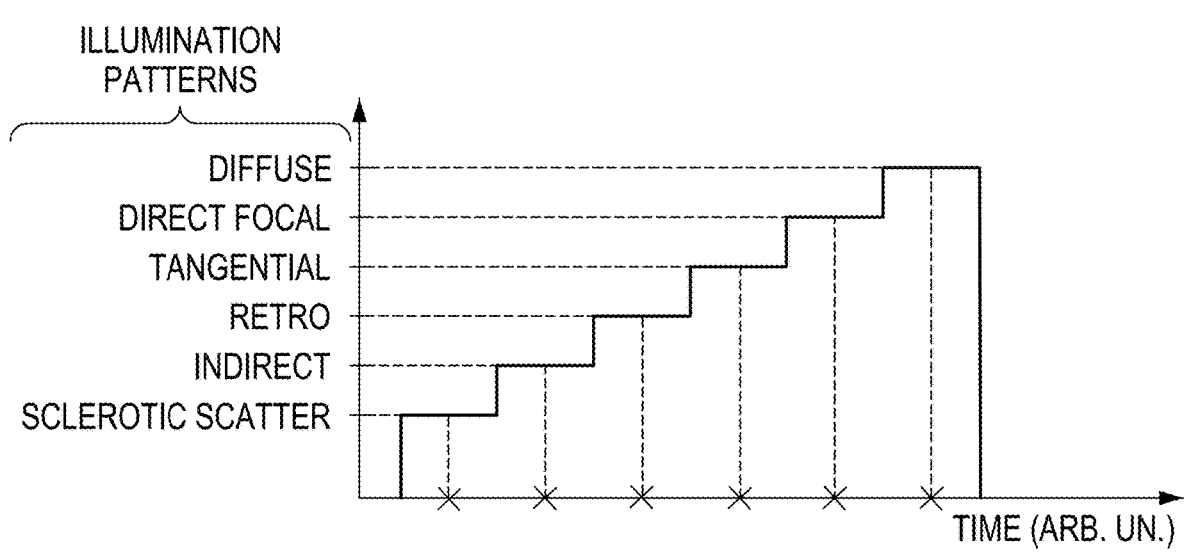
FIG. 3A is a graph showing illumination patterns used as a function of time in the method of FIG. 3, in accordance with one or more embodiments.

FIG. 3A shows an example of a given sequence 308 of illumination patterns. In this example, the sequence 308 includes six different illumination patterns in the following order: sclerotic scatter illumination, indirect illumination, retroillumination, tangential illumination, direct focal illumination and diffuse illumination. As shown, the crosses x represent moments in time where an image of the eye of the patient is generated by the image generation module 306. Accordingly, in this example, a first image of the eye is generated when illuminated according to sclerotic scatter illumination, a second image of the eye is generated when illuminated according to indirect illumination, a third image of the eye is generated when illuminated according to retroillumination, a fourth image of the eye is generated when illuminated according to tangential illumination, a fifth image of the eye is generated when illuminated according to direct focal illumination and a sixth image of the eye is generated when illuminated according to diffuse illumination. As will be appreciated, one or more images can be generated for each of the illumination patterns of the sequence 308 as need be. In some other embodiments, the order of the illumination patterns may differ from the order shown in FIG. 3A.

Figure 3B:
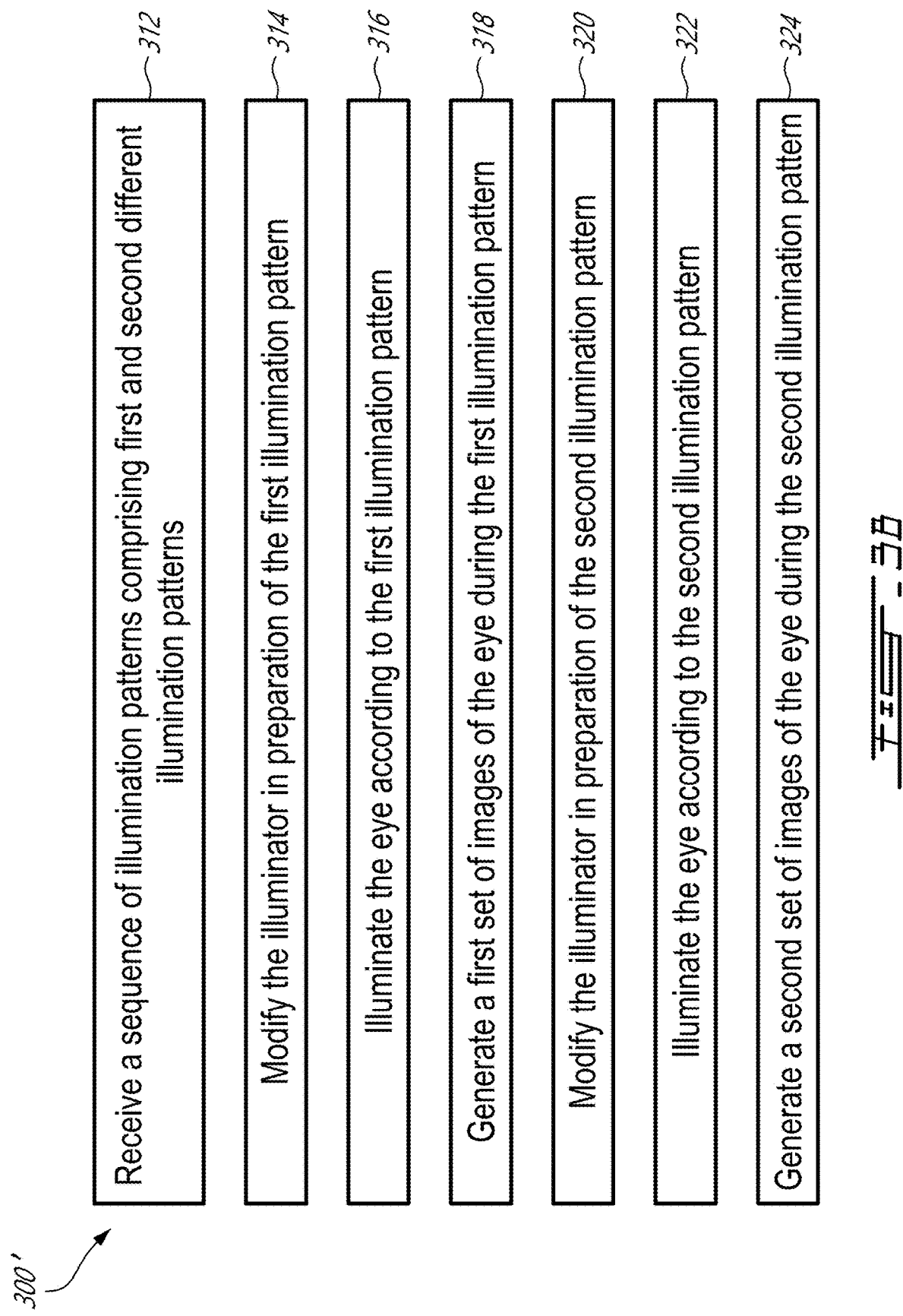
FIG. 3B is a flow chart of the method of FIG. 3, in accordance with one or more embodiments.

FIG. 3B shows an exemplary method 300' of imaging the eye 10 of the patient 12 received at the face receiving assembly 104 of the automated slit lamp system 100. The method 300' may be performed by running the software application 300 described with reference to FIG. 3A. Reference to the automated slit lamp system 100 of FIG. 1 is made for ease of reading.

At step 312, the controller 112 receives a sequence of illumination patterns comprising at least first and second illumination patterns being different from another, in which the first and second illumination patterns are selected from a group comprising: diffuse illumination, direct focal illumination, tangential illumination, retroillumination, indirect illumination and sclerotic scatter illumination.

At step 314, the controller 112 modifies the illuminator 106 of the slit lamp system 100 in preparation of the first illumination pattern.

At step 316, the illuminator 106 illuminates the eye 10 according to the first illumination pattern.

At step 318, the camera 108 generates a first set of images of the eye 10 during the first illumination pattern.

At step 320, the controller 112 modifies the illuminator 106 of the slit lamp system 100 in preparation of the second illumination pattern.

At step 322, the illuminator 106 illuminates the eye 10 according to the second illumination pattern.

At step 324, the camera 108 generates a second set of images of the eye 10 during the second illumination pattern.

In some embodiments, the controller 112 can associate the first set of images to the first illumination pattern and also associate the second set of images to the second illumination pattern. To do so, the controller 112 may generate time stamps indicating beginnings and/or ends of the first and second illumination patterns so that said association can be performed based on the time stamps. Additionally or alternately, it is noted that the controller 112 may generate one or more spatial stamps for each of the acquired images, the spatial stamps being indicative of the position(s) of the camera 108 and/or of the illuminator 106 when the corresponding image was acquired. As the position(s) of the camera 108 and/or of the illuminator 106 are known for each of the first and second illumination patterns, the controller 112 can associate each of the acquired images to either one of the first and second illumination patterns based on the spatial stamps.

It is envisaged that, in some embodiments, the sequence of illumination patterns can include a third illumination pattern, in which the third illumination pattern is selected from a group comprising: diffuse illumination, direct focal illumination, tangential illumination, retroillumination, indirect illumination and sclerotic scatter illumination. The first, second and third illumination patterns are different from one another in this embodiment. In such embodiments, the controller 112 can modify the illuminator 106 in preparation of the third illumination pattern, the illuminator 106 can then illuminate the eye 10 according to the third illumination pattern while the camera 108 generates a third set of images of the eye during the third illumination pattern. It is noted that the sequence of illumination patterns can include other illumination patterns as well.

The computing device 200 and the software application 300 described above are meant to be examples only. Other suitable embodiments of the controller 112 can also be provided, as it will be apparent to the skilled reader. For instance, in some embodiments, the controller 112 can be trained using machine-learning techniques to output diagnostic data based on the acquired images. In such embodiments, the controller 112 may determine which one of the illumination patterns is to be produced next based on the previously determined diagnostic data. Accordingly, examination of the eye of the patient can be performed in a fully automated manner.

It will be understood that the sequence of illumination patterns can differ from one embodiment to another. More specifically, some sequences of illumination patterns can have two different illumination patterns whereas some other sequences of illumination patterns can have three or more different illumination patterns. The number of illumination patterns in the sequence can thus vary.

As discussed above, the illumination patterns that can be sequentially produced by the illuminator of FIG. 1 can vary from one embodiment to another. Examples of such illumination patterns can include diffuse illumination, direct focal illumination, indirect illumination, retroillumination, sclerotic scatter illumination, three-mirror contact lens illumination, 90-diopter lens illumination and the like.

These types of illumination patterns are well-known in the art. However, for the sake of exhaustiveness, these types of illumination are described in the following paragraphs. Again, reference to the automated slit lamp system 100 of FIG. 1 is made for ease of reading.

Diffuse illumination 400 is obtained by increasing a width w of the slit illumination beam produced by the slit illuminator 106a. A so-increased illumination beam can be referred to as an "open illumination beam." Moreover, so as to diffuse the open illumination beam, a diffuser 402 is disposed across the open illumination beam. Accordingly, in the system of FIG. 1, the diffuser 402 can be movable between an on-path position in which the diffuser 402 lies across a path of the open illumination beam and an off-path position in which the diffuser 402 lies away from the path of the open illumination beam. In some embodiments, a background illuminator 106b can be used in conjunction with the slit illuminator 106a for more uniform lighting. It is sought that diffuse illumination may be normally used for overview images of the eye with low magnification such as with magnification of 10× or 16×.

FIGS. 4A and 5A show the illuminator 106 in two different variants of diffuse illumination patterns.

More specifically, FIG. 4A shows the illuminator 106 illuminating the eye 10 with diffuse illumination 400 so as to allow images of the overview of the eye, including the eyelids and eyelashes, to be generated. As shown in this specific example, the magnification of the camera 106 can be set to for example 10× or 16×, the width w of the slit illumination beam produced by the slit illuminator 106a can be set to maximum, the incidence angle of the slit illumination beam relative to the sagittal plane of the eye can be set to for example about 45 degrees, the intensity level of the slit illumination beam can be set to for example 4 on a scale of 0 to 10, the intensity level of the background illumination beam produced by the background illuminator 106b can be set to for example 3 on a scale of 1 to 7, and the aperture of the camera 108 can be set to for example 6 on a scale of 0 to 10. It is envisaged that such values are meant to be exemplary only as they can be set to other values relative to the scales alluded to above, or relative to any other suitable scale. For instance, the intensity of the slit illumination beam can be proportional to its width, which can vary continuously between for example 0 mm and 8 mm or more, in some embodiments. In some other embodiments, the intensity of the slit illumination beam can be selected among a plurality of pre-set intensities or from a continuous range of intensities, e.g., via a potentiometer. The intensity of the background illumination beam may vary between seven pre-set intensities, e.g., i) 100%, ii) 50% iii) 25% iv) 10% v) 5% vi) 0%, and vii) blue filter. Similarly, the intensity of the background illumination beam can be selected among a plurality of pre-set intensities or from a continuous range of intensities, e.g., via a potentiometer. FIG. 4B shows an exemplary image of an eye 10 of a patient generated when the eye is illuminated with such diffuse illumination 400. As can be appreciated, such diffuse illumination can give a shadow-free illumination showing natural colours and two light reflexes, which can be useful for low magnification overview images of the eye.

FIG. 5A shows the illuminator illuminating the eye with diffuse illumination 500 so as to allow images of a conjunctiva of the eye 10 to be generated. As shown in this particular embodiment, the magnification of the camera 108 can be set to for example 10× or 16×, the width of the slit illumination beam produced by the slit illuminator 106a can be set to maximum, the incidence angle of the slit illumination beam relative to the sagittal plane of the eye can be set to for example about 45 degrees, the intensity level of the slit illumination beam can be set to for example 3, the intensity level of the background illumination beam produced by the background illuminator 106b can be set to for example 3, and the aperture of the camera 108 can be set to for example 6. The scales with which these values are compared are the same as the ones described above. FIG. 5B shows an exemplary image of an eye 10 of a patient generated when the eye is illuminated with such diffuse illumination 500. It is intended that such diffuse illumination can provide evenly balanced lighting, with exposure control being more varied due to increased reflectivity.

Direct focal illumination typically refer to projecting the slit illumination beam on an ocular target at the plane of focus of the slit illumination beam. Unlike diffuse illumination, the so-focused slit illumination beam can penetrate transparent structures of the eye. When the slit illumination beam is centred, the resulting illumination is always direct focal illumination.

FIGS. 6A, 7A and 8A show the illuminator 106 in two different variants of direct focal illumination patterns.

More specifically, FIG. 6A shows the illuminator 106 illuminating the eye 10 with narrow direct focal illumination 600 so as to allow images of the cornea of the eye 10 to be generated. As shown in this specific example, the magnification of the camera 108 can be set to for example 16× or 25×, the width of the slit illumination beam produced by the slit illuminator 106a can be set to for example below 2 mm, the incidence angle of the slit illumination beam relative to the sagittal plane of the eye can be set to for example about above 60 degrees, the intensity level of the slit illumination beam can be set to for example 10, the intensity level of the background illumination beam produced by the background illuminator 106b can be set to for example 1, and the aperture of the camera 108 can be set to for example 3. FIG. 6B shows an exemplary image of an eye 10 of a patient generated when the eye is illuminated with such narrow direct focal illumination 600. Typically, a narrow direct focal illumination involves projecting the slit illumination beam at for example an angle or about 45 degrees to about 60 degrees relative to the sagittal plane of the eye. The slit illumination beam thereby cuts an optical section through the cornea like a knife. With such narrow direct focal illumination, it may be possible to locate layers of pathological changes.

FIG. 7A shows the illuminator illuminating the eye 10 with narrow direct focal illumination 700 so as to allow images of a lens of the eye 10 to be generated. As shown in this particular embodiment, the magnification of the camera 108 can be set to 16× or 25×, the width of the slit illumination beam produced by the slit illuminator 106a can be set to for example below 0.2 mm, the incidence angle of the slit illumination beam relative to the sagittal plane of the eye can be set to for example about above 60 degrees, the intensity level of the slit illumination beam can be set to for example 10, the intensity level of the background illumination beam produced by the background illuminator 106b can be set to for example 1, and the aperture of the camera 108 can be set to for example 4. FIG. 7B shows an exemplary image of an eye 10 of a patient generated when the eye is illuminated with such narrow direct focal illumination 700. It is intended that such diffuse illumination 700 can provide evenly balanced lighting, with exposure control being more varied due to increased reflectivity. Such narrow slit illumination beam is projected at an angle of for example about 45 degrees to the lens as an optical section is made. Due to the problematic depth of field it is not possible to image the entire lens section in focus. It is therefore required, in some embodiments, to focus on either an anterior or posterior lens surface. Such a narrow direct focal illumination pattern 700 can include imaging the anterior lens surface and then imaging the posterior lens surface, depending on the embodiment.

The lens can also be imaged with moderate direct focal illumination 800, such as shown in FIG. 8A. In this example, the magnification of the camera 108 can be set to for example 16× or 25×, the width of the slit illumination beam produced by the slit illuminator 106a can range between 2 mm and 4 mm, the incidence angle of the slit illumination beam relative to the sagittal plane of the eye 10 can be set to about above 60 degrees, the intensity level of the slit illumination beam can be set to for example 10, the intensity level of the background illumination beam produced by the background illuminator 106b can be set to for example 1, and the aperture of the camera 108 can be set to for example 6. FIG. 8B shows an exemplary image of an eye 10 of a patient generated when the eye is illuminated with such moderate direct focal illumination 800. In such moderate direct focal illumination 800, the slit illumination beam may be projected at about 45 degrees from the lens pathology and is directly illumination thereby.

Tangential illumination, often times referred to as "specular reflection," or "reflected illumination" is achieved by projecting a slit illumination beam of narrow or moderate width, albeit thicker than an optical section, towards the eye from the temporal side. The incidence angle is preferably wide, e.g., about 50 degrees to 60 degrees relative to the sagittal plane of the eyen, which should be slightly nasal to the patients visual axis in this embodiment. A bright zone of specular reflection will appear on the temporal, midperipheral corneal epithelium, and it can be used to see endothelial outline of cornea.

More specifically, FIG. 9A shows the illuminator illuminating the eye 10 with tangential illumination 900 so as to allow images of the cornea of the eye 10 to be generated. As shown in this specific example, the magnification of the camera 108 can be set to for example 16× or 25×, the width of the slit illumination beam produced by the slit illuminator 106a can be set to above 4 mm, the incidence angle of the slit illumination beam relative to the sagittal plane of the eye can be set to about above 60 degrees, the intensity level of the slit illumination beam can be set to for example 10, the intensity level of the background illumination beam produced by the background illuminator 106b can be set to for example 0, and the aperture of the camera 108 can be set to for example 6. FIG. 9B shows an exemplary image of an eye 10 of a patient generated when the eye is illuminated with such tangential illumination 900. This illumination pattern can provide more information as the oblique illumination is reflected and refracted on any pathology. The width of the slit illumination beam can be swept in the narrow and moderate ranges for optimal results.

The iris can also be imaged with tangential illumination 900, such as shown in FIG. 10A. In this example, the magnification of the camera 108 can be set to for example 16× or 25×, the width of the slit illumination beam produced by the slit illuminator 106a can be wide open, the incidence angle of the slit illumination beam relative to the sagittal plane of the eye can be set to about above 60 degrees, the intensity level of the slit illumination beam can be set to for example 10, the intensity level of the background illumination beam produced by the background illuminator 106b can be set to for example 0, and the aperture of the camera 108 can be set to for example 6. FIG. 10B shows an exemplary image of an eye 10 of a patient generated when the eye is illuminated with such tangential illumination 900. In such tangential illumination, the open illumination beam can be projected at an angle of about 80 degrees to about 90 degrees relative to the sagittal plane of the eye and onto the iris. Such tangential illumination can create strong shadows and the surface texture may be enhanced. In some circumstances, it may be useful to display an instruction to turn the patient's head a little away from the light during examination.

Indirect illumination generally involves projecting the slit illumination beam of moderate width (between 2 to 4 mm) besides the pathology or ocular portion under examination. More specifically, the slit illumination beam may be decentred to not directly fall on the pathology or ocular portion to be imaged. As such, the decentred illumination beam is projected just adjacent to the subject area and it is illuminated by scattered internally reflected light. The axes of illuminating and viewing path do not intersect at the point of image focus. To do so, the illuminating prism is decentered by rotating it about its vertical axis off the normal position. In this way, reflected, indirect light illuminates the area of the anterior chamber or cornea to be examined. The observed corneal area then lies between the incident light section through the cornea and the irradiated area of the iris. Observation can thus be allowed against a comparatively dark background.

Retroillumination also involves a decentred slit illumination beam. As such, retroillumination can be considered a form of indirect illumination. With this illumination pattern, light reflected from the fundus or iris illuminates the pathology from behind. If the slit illumination beam is decentred and higher magnification is used, unwanted reflections can be minimized.

FIG. 11A shows the illuminator illuminating the eye with retroillumination 1100 so as to allow images of the cornea of the eye 10 to be generated. As shown in this specific example, the magnification of the camera 108 can be set to for example 16× or 25×, the width of the slit illumination beam produced by the slit illuminator 106a can be set to between 1 mm and 3 mm, the incidence angle of the slit illumination beam relative to the sagittal plane of the eye can be set to about 45 degrees in a decentred manner, the intensity level of the slit illumination beam can be set to for example 10, the intensity level of the background illumination beam produced by the background illuminator can be set to for example 0, and the aperture of the camera 108 can be set to for example 5. FIG. 11B shows an exemplary image of an eye 10 of a patient generated when the cornea is illuminated with such retroillumination 1100. By using a slit illumination beam of moderate width and by projecting it onto the iris behind a potential pathology of the cornea, the slit illumination beam reflects on the iris and backlights the cornea. If there is some cataract present on the lens, the lens can also be used to reflect light directly onto an area of interest of the cornea.

The lens can also be imaged with retroillumination 1100, such as shown in FIG. 12A. In this example, the magnification of the camera 108 can be set to for example 16×, 25× or 40×, the width of the slit illumination beam produced by the slit illuminator 106a can range between 1 mm and 2 mm, the incidence angle of the slit illumination beam relative to the sagittal plane of the eye 10 can be set to about below 5 degrees, the intensity level of the slit illumination beam can be set to for example 5, the intensity level of the background illumination beam produced by the background illuminator 106b can be set to for example 0, and the aperture of the camera 108 can be set to for example 5. FIG. 12B shows an exemplary image of an eye 10 of a patient generated when the lens is so-retroilluminated. In such retroillumination, the slit illumination beam can be positioned in an almost coaxial position with the camera 108. When the slit illumination beam of wide width is decentred and adjusted to half circle by using the slit width and height controls, the decentred slit illumination beam can be projected near the pupil margin through a dilated pupil.

Other types of illumination patterns may require the automated slit lamp system to use three-mirror contact lens or 90-diopter lens. With these lenses, there are more optical interfaces (air/glass and glass/cornea). Accordingly, all these interfaces cause reflexes and therefore it is better to take images without the background illumination. Furthermore, any scratches or damage to the lens will increase the number of image artefacts. If the space between the diagnostic contact lens and the slit illuminator is very small, the background illuminator can be locked in the centre position.

FIG. 13A shows the illuminator illuminating the eye with 90-diopter lens illumination 1300 so as to allow images of the fundus of the eye to be generated. As shown in this specific example, the magnification of the camera 108 can be set to for example 10× or 16×, the width of the slit illumination beam produced by the slit illuminator 106a can be set to between 2 mm and 4 mm, the incidence angle of the slit illumination beam relative to the sagittal plane of the eye can be set to below 30 degrees, the intensity level of the slit illumination beam can be set to for example 5, the intensity level of the background illumination beam produced by the background illuminator can be set to for example 0, and can be set to for example 5. FIG. 13B shows an exemplary image of an eye 10 of a patient generated when the fundus is illuminated with such 90-diopter lens illumination 1300. In this illumination pattern, a slit illumination beam of moderate width with an almost co-axial incidence may be satisfactorily used.

Figure 14A:
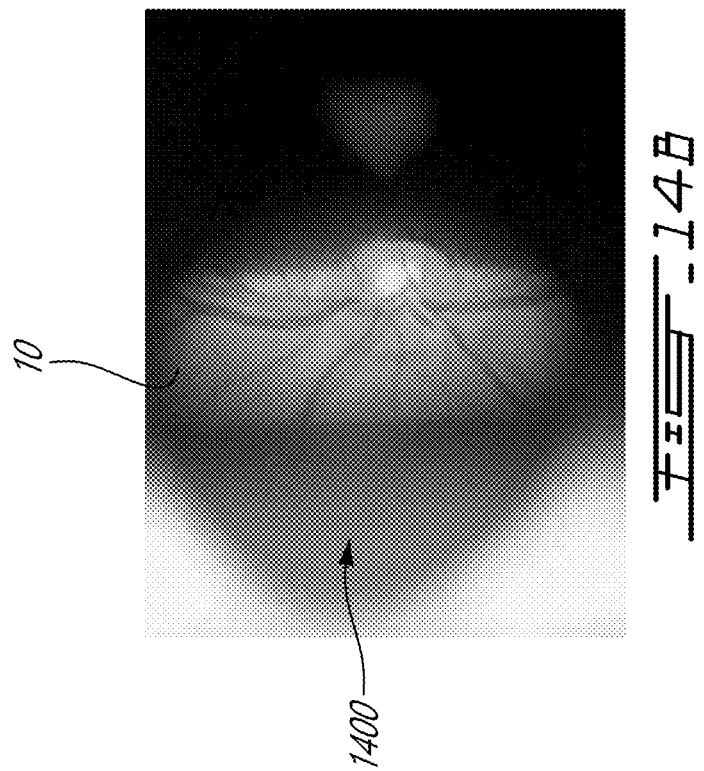
FIG. 14A is a top plan view of an example of an automated slit lamp system, shown in a three-mirror contact lens illumination pattern, in accordance with one or more embodiments.
Figure 14B:
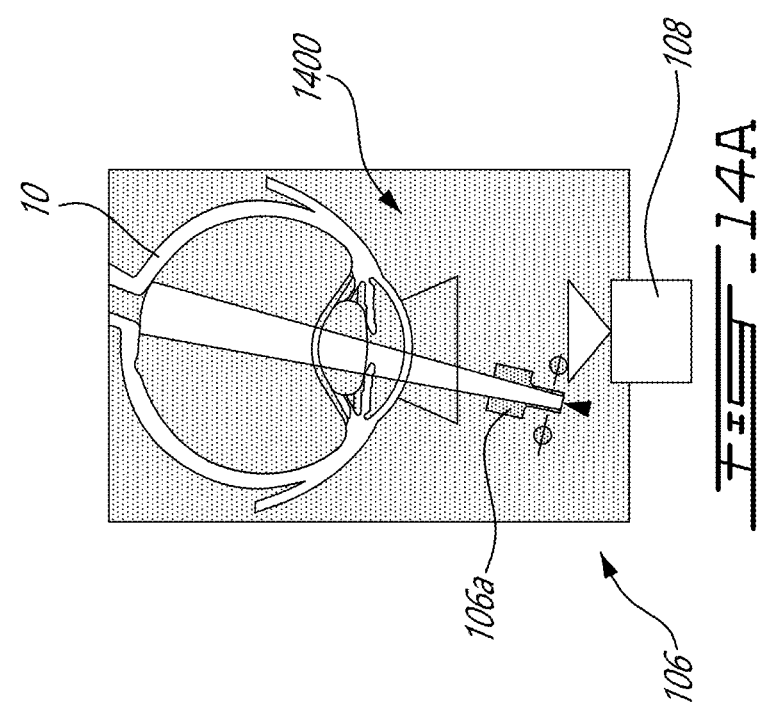
FIG. 14B is an exemplary image of an eye generated during the three-mirror contact lens illumination pattern of FIG. 14A.

The fundus can also be imaged with three-mirror contact lens illumination 1400, such as shown in FIG. 14A. In this example, the magnification of the camera 108 can be set to for example 10×, 16×, 25× or 40×, the width of the slit illumination beam produced by the slit illuminator 106a can be set to about 2 mm, the incidence angle of the slit illumination beam relative to the sagittal plane of the eye can be set to about below 30 degrees, the intensity level of the slit illumination beam can be set to for example 5, the intensity level of the background illumination beam produced by the background illuminator can be set to for example 0, and the aperture of the camera 108 can be set to for example 5. FIG. 14B shows an exemplary image of an eye 10 of a patient generated when the fundus is so-illuminated. As shown, the slit illuminator 106a can be positioned in an almost coaxial position with the camera 108. A wide slit beam is decentered and adjusted to a half circle by using the slit width and height controls. The decentred slit beam is projected near the pupil margin through a dilated pupil.

In some other embodiments, sclerotic scatter can be used. With this type of illumination, a wide light beam is projected directed onto a limbal region of the cornea at an extremely low angle of incidence and with a laterally de-centered illuminating prism. Adjustment must allow the light beam to transmit through the corneal parenchymal layers according to the principle of total reflection allowing the interface with the cornea to be brightly illuminated. The magnification should be selected so that the entire cornea can be seen.

As can be understood, the examples described above and illustrated are intended to be exemplary only. It is noted that the face receiving assembly described in the illustrated embodiment may be omitted in some other embodiments. For instance, the automated slit lamp system can be partially or wholly part of a portable electronic device, such as a smart phone, an electronic tablet, a hand-type scanner and the like, which can be moved proximate to the face of the patient for examination. In such embodiments, the face of the patient would not necessarily need to be received in a face receiving assembly, as the illumination could occur in a free-standing fashion. However, it is also envisaged that a face receiving assembly can be mounted to a portable electronic device in some other embodiments, to immobilize the face of the patient relative to the portable electronic device. For instance, the portable electronic device can be provided in the form of a headset which can be worn on the head of the patient. It is noted that in some embodiments, the automated slit lamp system can have an indicator which is generally mounted to the frame and proximate to the illuminator. The indicator may be removably or fixedly mounted to the frame using, for instance, one or more mounts. The indicator can be provided in the form of any visual indicator such as a display screen of a mobile electronic device, an auditory indicator, a haptic indicator and the like. The indicator can be configured to indicate within a surrounding environment predetermined parameters associated to a given illumination pattern, wherein when the adjustable parameters of a manually adjustable illuminator are manually set to the predetermined parameters the manually adjustable illuminator illuminates the eye of the patient with the given illumination pattern. In these embodiments, the controller can be communicatively coupled to either one of the indicator and the illuminator, or both. The controller may control the indicator to indicate a first series of predetermined parameters of the illuminator for illumination of the eye of the patient according to a first illumination pattern; and after that the controller may control the indicator to indicate a second series of predetermined parameters of the illuminator for illumination of the eye of the patient according to a second illumination pattern, with the first and second illumination patterns being different from one another. In some embodiments, an operator may modify the adjustable parameters of the illuminator based on the indicated parameters on a manual basis. However, the indication of the predetermined parameters can be made for training purposes only, as the illuminator may still be automatically controlled via the controller in some embodiments, thereby requiring no or almost no operator intervention. Communication between the automated slit lamp system and one or more remote databases comprising an electronic medical record of the patient can be wired, wireless or a combination thereof. In some other embodiments, the illuminator can comprise an array of light emitting elements (e.g., light emitting diodes) which can be selectively activatable by the controller to provide either slit illumination, background illumination, or both depending on the desired illumination pattern. The set of images can include one or more images. In some embodiments, the camera automatically moves in one or more axes, namely the X, Y and Z axes, relative to the frame in order to generate image(s) of the eye. The movement of the camera may be function of the illumination pattern of the illuminator. For instance, in some embodiments, the camera may be moved to a first position for generating an image of the eye during illumination in a first illumination pattern, the camera may be moved to a second position (which may or may not be different to the first position) for generating an image of the eye during illumination in a second illumination pattern, and so forth. The movement of the camera may be performed via robotized elements such as robot arm(s), conveyor(s) or actuator(s). These robotized elements may be communicatively coupled to the controller which may automatically control the movement of the camera on the basis of the current illumination pattern. In some embodiments, the illuminator is provided in the form of a slit illuminator. In some other embodiments, the illuminator is provided in the form of a background illuminator. The illuminator can include both a slit illuminator and a background illuminator. In some embodiments, the slit illuminator and/or background illuminator may be automatically controlled by the controller to perform any of the sought illumination patterns. The slit illuminator may be precisely controllable to illumination correspondingly precise portions of the eye, such as the junction between the iris and the sclera, in some embodiments. The scope is indicated by the appended claims.

What is claimed is:

1. An automated slit lamp system for imaging an eye of a patient, the automated slit lamp system comprising:
   a frame;
   an illuminator mounted to the frame and emitting an illumination beam towards the eye of the patient, the illuminator being operable to illuminate the eye of the patient in a plurality of different illumination patterns;
   a controller communicatively coupled to the illuminator, the controller having a processor and a memory having stored thereon instructions which when executed by the processor perform the steps of: controlling the illuminator to illuminate the eye of the patient with a sequence of illumination patterns comprising at least a first illumination pattern and a second illumination pattern being different from the first illumination pattern, the first and second illumination patterns being selected from a group comprising: diffuse illumination, direct focal illumination, tangential illumination, retroillumination, indirect illumination and sclerotic scatter illumination; and
   a camera mounted to the frame and generating a plurality of images of the eye during both the first and second illumination patterns;
   wherein the controller is communicatively coupled to the camera, the instructions further comprising: receiving the plurality of images from the camera; associating a first set of the received images to the first illumination pattern, associating a second set of the received images to the second illumination pattern, and generating time stamps indicating at least one of beginnings and ends of the first and second illumination patterns, said associating being performed based on said time stamps.

2. The automated slit lamp system of claim 1 wherein the camera is a three-dimensional camera.

3. The automated slit lamp system of claim 2 wherein the three-dimensional camera is a light field imaging camera or stereo-camera.

4. The automated slit lamp system of claim 1 wherein said sequence of illumination patterns further comprises a third illumination pattern being different from the first and second illumination patterns, the third illumination pattern being selected from a group comprising: diffuse illumination, direct focal illumination, tangential illumination, retroillumination, indirect illumination and sclerotic scatter illumination.

5. The automated slit lamp system of claim 4 wherein said sequence of illumination patterns further comprises a fourth illumination pattern being different from the first, second and third illumination patterns, the fourth illumination pattern being selected from a group comprising: diffuse illumination, direct focal illumination, tangential illumination, retroillumination, indirect illumination and sclerotic scatter illumination.

6. The automated slit lamp system of claim 1 further comprising a face receiving assembly mounted to the frame and receiving a face of the patient.

7. The automated slit lamp system of claim 6 further comprising an eye sensor mounted to the frame, the eye sensor detecting a presence of the face of the patient in said face receiving assembly, and generating a signal indicating that said sequence of illumination patterns can be initiated.

* * * * *